United States Patent [19]
Dürr et al.

[11] Patent Number: 5,122,135
[45] Date of Patent: Jun. 16, 1992

[54] APPARATUS FOR THE SURGICAL TREATMENT OF A POINT SITUATED IN AN EYE

[75] Inventors: Ulrich Dürr, Steffisburg; Taoufik Nouri, Oberhofen; Jürg Steinger, Arnisäge, all of Switzerland

[73] Assignee: Lasag AG, Thun, Switzerland

[21] Appl. No.: 417,703

[22] Filed: Oct. 5, 1989

[30] Foreign Application Priority Data

Oct. 6, 1988 [CH] Switzerland ............... 03745/88

[51] Int. Cl.$^5$ ............... A61H 5/06
[52] U.S. Cl. ............... 606/4; 606/6; 606/18; 128/395
[58] Field of Search ............... 128/395, 387, 398; 606/4, 6, 10, 13–14

[56] References Cited

U.S. PATENT DOCUMENTS

| | | | |
|---|---|---|---|
| 4,391,275 | 7/1983 | Fankhauser | 606/4 |
| 4,520,816 | 6/1985 | Schachar et al. | 128/303.1 |
| 4,573,467 | 3/1986 | Rich et al. | 128/303.1 |
| 4,576,160 | 3/1986 | Tanaka | 606/10 |
| 4,628,416 | 12/1986 | Dewey | 606/16 |
| 4,732,460 | 3/1988 | Kele et al. | 606/4 |
| 4,862,886 | 9/1989 | Clarke et al. | 606/17 |

FOREIGN PATENT DOCUMENTS

8705794 8/1987 PCT Int'l Appl.

Primary Examiner—Stephen C. Pellegrino
Assistant Examiner—David Shay
Attorney, Agent, or Firm—Griffin, Branigan & Butler

[57] ABSTRACT

An apparatus having a first generator designed to produce a first beam of coherent light, the energy of which is concentrated in a succession of impulses each capable causing a microexplosion in organic tissue at the point to be treated, a second generator designed to produce a second beam of coherent light able to penetrate the thickness of this organic tissue, an optical system designed to focus the first or the second beam on the point to be treated and a beam switch able to selectively direct the first or the second beam towards the optical system. The second beam enables ophthalmologists to perform operations that could not hiterto be performed with know apparatuses, notably operations involving the penetration of a treatment beam into the thickness of the tissues of the eye.

10 Claims, 5 Drawing Sheets

APPARATUS FOR THE SURGICAL TREATMENT OF A POINT SITUATED IN AN EYE

BACKGROUND OF THE INVENTION

Apparatus for the surgical treatment of a point situated in an eye that are currently available generally have two generators each producing a beam of coherent light.

The first of these generators has a powerful laser, for example a laser having as active medium a bar of yttrium and aluminum garnet doped with neodymium (generally termed a Nd:YAG laser) which produces a beam of coherent infrared light having a wavelength of 1.06 micrometers. This laser is associated with what specialists refer to as a "Q-switch".

This Q-switch is composed of an electrooptical cell, for example a Pockels cell, arranged in the resonant cavity of the laser and able to change the factor of quality Q of this resonant cavity (hence its name "Q-switch")in such a way that all the light energy produced by the laser is concentrated in successive, very short, impulses of a few nanoseconds' duration.

When a beam of coherent light produced by a generator of this kind is focussed on a point to be treated in an eye, each impulse causes a micro-explosion which destroys the material present at that point.

The second generator of the known apparatus has a laser in the resonant cavity of which light waves can oscillate freely, that is, without a "Q-switch".

The beam of coherent light produced by this second generator is essentially designed to coagulate blood which could be discharged in the eye. The active medium of the laser of this second generator is therefore chosen so that this coherent light is well absorbed by the red pigment in the blood. An active medium of this kind is, for example, argon, in which case the coherent light emitted has a wavelength of between 488 and 514 nanometers, that is to say a colour ranging from blue to green, which can be chosen by the ophthalmologist.

Since it is absorbed by the blood which is present in all the tissues of the eye, the beam of coherent light produced by the second generator of the known apparatus only penetrates a short distance into these tissues. It cannot therefore be used when the operation to be carried out calls for the beam of coherent light to penetrate relatively deeply into the tissue of the eye.

Laboratory experiments and clinical trials have shown that operations of this type can be advantageously carried out with the aid of a beam of coherent light having a wavelength similar to that of the light emitted by lasers, the active medium of which is a bar of yttrium and aluminium garnet doped with neodymium when this beam is continuous or composed of relatively long impulses, that is when the laser producing this beam is not associated with a Q-switch.

In this context, reference is made for example to the book entitled "Neodymium : YAG Laser Microsurgery : Fundamental Principles and Clinical Applications", edited by R. M. Klapper, published by Little, Brown and Co in Boston (USA) and, more specifically, to the chapters "Microsurgery with the Neodymium : YAG Laser : An Overview" by F. Fankhauser and P. Rol, and "Neodymium : YAG Laser Capsulotomy", by T. A. Deutsch and M. F. Goldberg.

In order to perform all possible microsurgical operations, an ophthalmologist should therefore have an installation comprising, on the one hand, a known apparatus such as that described hereinabove, used to perform the classic operations, and on the other hand, a generator producing a beam of continuous or pulsed coherent light of long wavelength having an optical system adapted to this generator with which, for example, the operations described in the above book can be carried out.

An installation of this type would be cumbersome and expensive.

OBJECTS OF THE INVENTION

It is an object of the present invention to provide an apparatus enabling an ophthalmologist to perform any desired microsurgical ophthalmological operation, this apparatus being less cumbersome and cheaper than the installation described above.

BRIEF SUMMARY OF THE INVENTION

This object is achieved by the claimed apparatus which comprises a first generator designed to produce a first beam of coherent light and having means to concentrate the energy of said first beam in a succession of impulses each capable of causing a microexplosion in the material at that point, and an optical system designed to focus said first beam on said point and which is characterized in that it has a second generator designed to produce a second beam of coherent light capable of penetrating into the thickness of said material, and a beam switch capable of selectively directing said first beam and said second beam along the axis of said optical system.

BRIEF DESCRIPTION OF THE DRAWINGS

Other features and advantages of the invention will emerge from the following description with reference to the drawings in which.

DETAILED DESCRIPTION OF THE INVENTION

Figure 1:
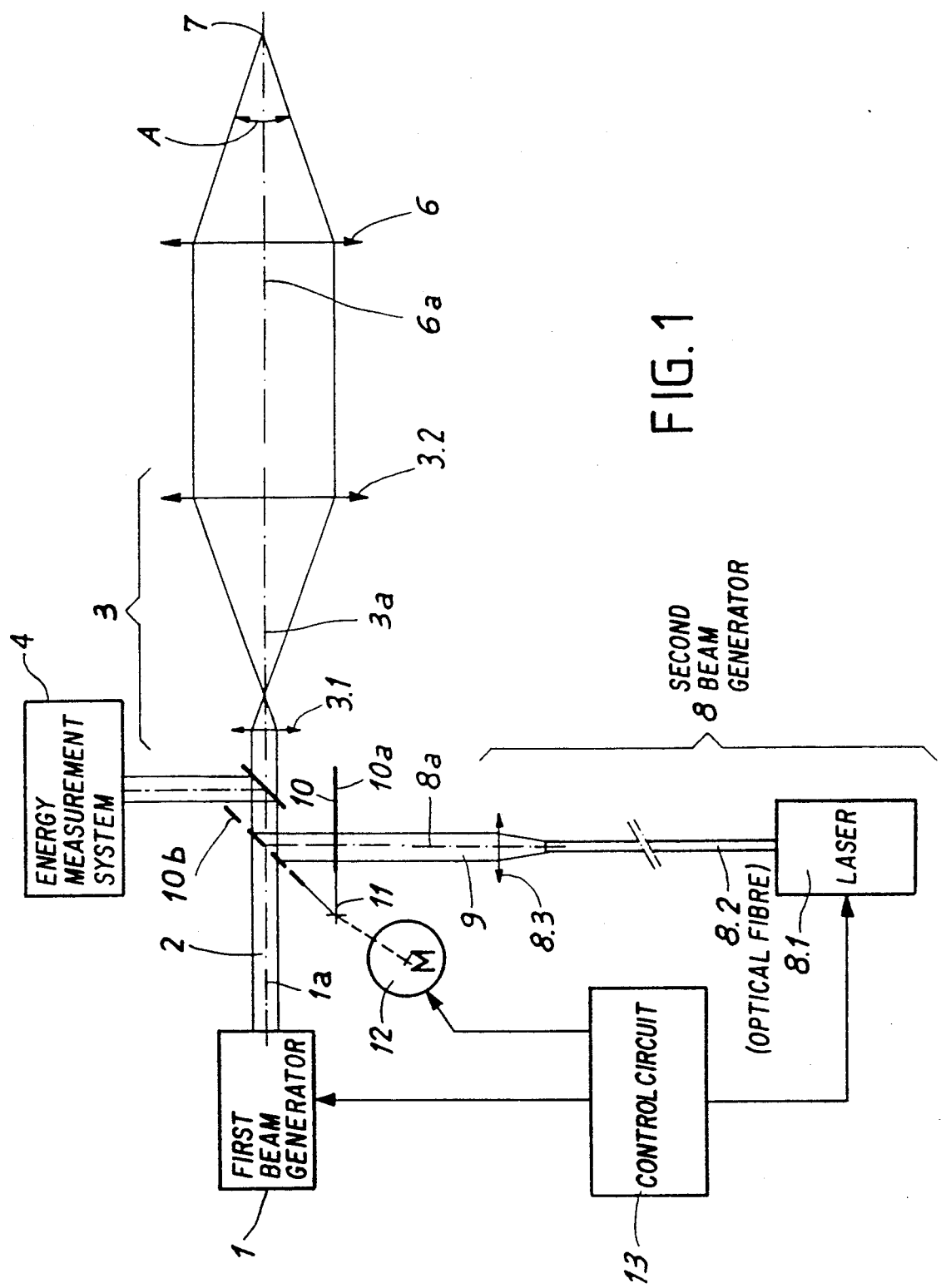
FIG. 1 is a diagrammatic representation of an embodiment of an apparatus according to the invention.

In the embodiment shown diagrammatically and as a non-limiting example in FIG. 1, the apparatus according to the invention has a first generator designated by the reference numeral 1.

This generator 1 is designed to produce a beam of coherent light 2 along an emission axis 1a, this beam 2 being composed of very short and very intense impulses capable of causing microexplosions at the point on which it is focussed and of destroying organic tissue present at this point, or any other material affecting the correct functioning of the eye.

As in the known apparatuses, this generator 1 can comprise a laser, the active medium of which is composed of a bar of yttrium and aluminium garnet doped with neodymium (Nd : YAG laser) associated with a Q-Switch and it will not be described in detail here.

The apparatus of FIG. 1 also has a telescope 3, the optical axis $3a$ of which coincides with the emission axis $1a$ of the generator 1 as well as an energy measurement system 4, realized for example by means of an Ulbricht ball and placed upstream of the telescope 3.

The telescope 3 is composed in conventional manner of two optical systems each symbolized by a single converging lens and designated by the reference numerals 3.1 and 3.2.

The apparatus of FIG. 1 has, in addition, a lens 6, also symbolized by a single converging lens, the optical axis $6a$ of which coincides with the optical axis $3a$ of the telescope and, thus, with the emission axis $1a$ of the generator 1.

The apparatus of FIG. 1 has in addition means, not shown, which make it possible to move the housing, not shown, in which are arranged the generator 1, the telescope 3 and the lens 6, in order to make the focal point 7 of the lens 6 coincide with the point to be treated. In that case, means could also be provided making it possible to move the lens 6 in relation to the housing.

As in the case of the above mentioned known apparatuses, the apparatus of FIG. 1 has a second generator, designated by the reference numeral 8. However, unlike the second generators of the known apparatuses, the generator 8 is designed to produce a beam of coherent light 9 having a wavelength sufficiently high to penetrate deeply into the tissues of the eye.

For example, the generator 8 can have a laser, the active medium of which is a bar of yttrium and aluminium garnet. doped with neodymium, similar to the laser of generator 1.

However, in contradistinction to the latter, the laser of the generator 8 does not have a Q-switch and is disposed so that the beam 9 emitted along the emission axis $8a$ of the generator 8 is, as desired, continuous or composed of impulses of a few milliseconds' duration.

Due to its mode of operation, the laser of the generator 8, which is designated by the reference number 8.1 in FIG. 1, gives off a considerable amount of heat during operation.

Consequently, this laser 8.1 cannot be fitted in the housing, not shown, which contains all the other parts of the apparatus which have hitherto been described.

The connection between the laser 8.1 and the rest of the apparatus is provided by an optical fibre 8.2, one end of which is coupled by means (not shown) to the laser 8.1 and the other end of which is fixed in the above-mentioned housing.

The beam of light emitted by this other end of the optical fibre 8.2 is divergent and the generator 8 has an optical system 8.3 so disposed that this diverging beam is rendered parallel and forms the beam 9.

In the example of FIG. 1, this optical system 8.3 is arranged so that its optical axis, which is the emission axis $8a$ of the generator 8, cuts the emission axis $1a$ of the generator 1 at a right angle.

The apparatus of FIG. 1 also has a beam switch symbolized by a mirror 10 capable of taking up two stable positions $10a$ and $10b$, for example by being rotated about an axis 11 by a motor 12 or by any other suitable electro-mechanical converter.

When in its position $10a$, the mirror 10 is arranged outside the path of the beam 2, so that this latter, when it is emitted by the generator 1, is able to reach the telescope 3.

When in its position $10b$, the plane of the mirror contains the point of intersection of the axes of emission $1a$ and $8a$ and makes an angle of 45° with each of these latter, so that the beam 9, when it is emitted by the generator 8, is reflected in the direction of the telescope 3 and that its axis, after this reflection, coincides with the optical axis $3a$ of this telescope 3.

Figure 2:
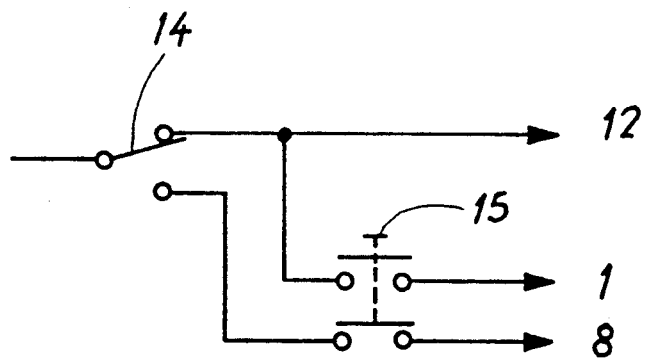
FIG. 2 is a diagram of an example of the control circuit of the apparatus of FIG. 1.

Finally, the apparatus of FIG. 1 has a control circuit 13, one very simplified example of which is shown in FIG. 2.

This control circuit 13 is connected to the generators 1 and 8 as well as to the motor 12 designed to move the mirror 10 from one to the other of its positions $10a$ and $10b$.

The control circuit 13 has a reversing switch 14 which can be placed manually into one or other of its two stable positions and a switch 15 having two contacts which can be closed by, for example, actuating a push-button, these two contacts opening again when this push-button is released.

In the position in which the reversing switch 14 is shown in FIG. 2, the mirror drive motor 12 is controlled so that the latter takes up its position $10a$ and, when the switch 15 is closed, the generator 1 comes into operation. This generator 1 then produces the beam 2, which is widened in the telescope 3, then focussed by the lens 6 on the point to be treated.

When the reversing switch 14 is put into its other stable position, the drive motor 12 of the mirror 10 is controlled so that this latter takes up its position $10b$. In this case, if the switch 15 is actuated, it is the generator 8 which comes into operation. The beam 9 which it produces is then reflected by the mirror 10 so that its axis coincides with the optical axis $3a$ of the telescope 3, widened by the telescope 3, then focussed by the lens 6 on the point to be treated.

The apparatus of FIG. 1 can moreover have means (not shown) enabling the optical system 4 to be moved along the axis $3a$ to unfocus the beam 2 or 9 and to change the diameter of the area of the eye which it reaches, making it possible to vary the density of the light energy in this area.

In the apparatus of FIG. 1, the angle of the top of the cone formed by the beam 2 or the beam 9 when it is focussed by the lens 6 is fixed.

In a well known manner and for a given telescope 3 and a lens 6, this angle, designated by A in FIG. 1, depends only on the diameter of the beam entering the telescope 3.

It will be assumed that, in the example of FIG. 1, the diameters of the beams 2 and 9 are equal and such that the angle A equals 16°, which is a commonly used value.

It is, however, well known that, depending on the type of operation to be carried out and depending on the position of the point to be treated in the eye, the ophthalmologist may require this angle to have a smaller value, typically 8°, notably when the beam which he wishes to use is the beam 9 produced by the generator 8.

FIG. 3 illustrates an embodiment of the apparatus of the invention in which it is possible to change the diameter of the beam 9 emitted by the generator 8.

In this embodiment, the optical system 8.3 is no longer fixed, but it is disposed on a moving support 16 which can be rotated about an axis 16a by a motor 17 to adopt one or the other of two well defined angular positions.

Figures 3A, 3B:
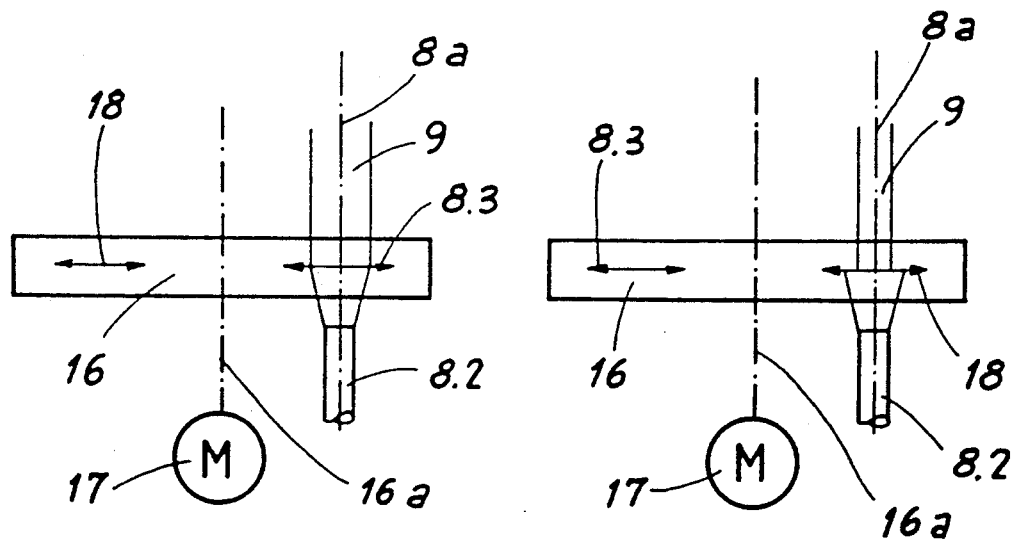
FIGS. 3A and 3B illustrate first and second positions, respectively, of a motor driven optical system for changing the diameter of a coherent beam of light generated by the beam generator 8 of FIG. 1.

In one of these positions, which is that shown in FIG. 3a, the optical system 8.3 occupies exactly the same place as that which it has in the apparatus of FIG. 1. The beam 9 therefore has the same diameter as in this latter apparatus and the angle A also equals 16°.

A second optical system, designated by 18, is mounted on the moving support 16 so that, when this latter is in its second angular position as illustrated in FIG. 3b, this optical system 18 is aligned with the optical fibre 8.2 and thus receives the diverging beam emerging therefrom.

The optical system 16 is so dimensioned that this diverging beam is made parallel and, moreover, that the diameter of this parallel beam, which in this case constitutes the beam 9, has the value for which the angle A equals 8°.

The motor 15 can of course be controlled by the ophthalmologist using suitable control means (not shown) forming part of the control circuit 13.

The other elements of this embodiment of the apparatus according to the invention are identical to those described with reference to FIG. 1. They have consequently not been shown again in this FIG. 3.

Figure 4:
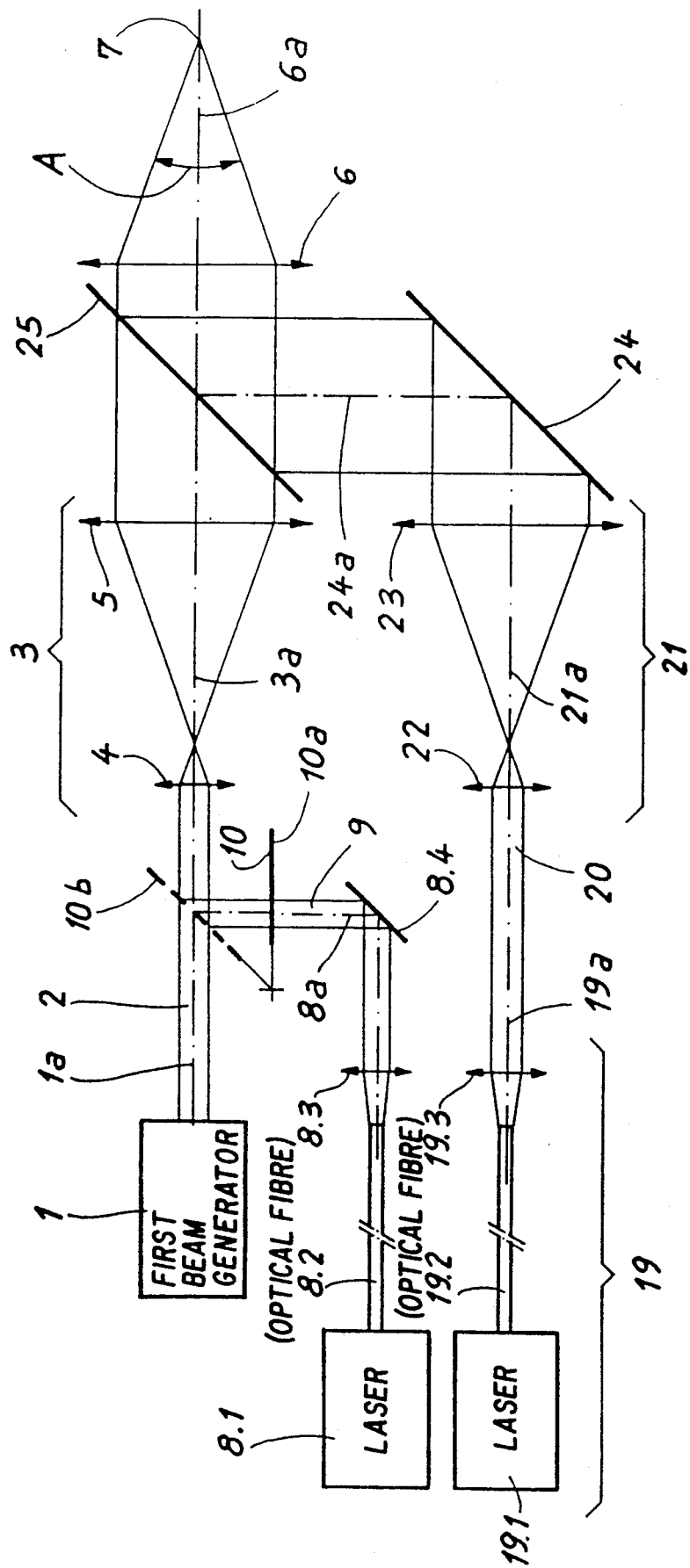
FIG. 4 is a diagrammatic representation of another embodiment of the apparatus according to the invention.

In the embodiment shown in FIG. 4, the apparatus according to the invention has the same elements as the apparatus of FIG. 1. These elements are designated by the same reference numerals as in this FIG. 1 and they will not be described again here. Only the motor 12 designed to move the mirror 10 from one to the other of its positions 10a and 10b and the control circuit 13 have not been shown in this FIG. 4 so as not to confuse the drawing unnecessarily.

Apart from the elements described hereinabove, the apparatus of FIG. 4 has a third generator 19 designed to produce a beam of coherent light having a wavelength that is readily absorbed by the red pigment of the blood.

As in the known apparatuses described hereinabove, this generator 19 can comprise a laser, the active medium of which is composed of argon, the light emitted by the generator having, in this case, a wavelength of between 488 and 514 nanometers.

As does the laser 8.1 of the generator 8, the laser of the generator 19, which is designated by 19.1, wastes a great deal of energy during operation and can consequently not be located in the housing (not shown) which contains the other elements of the apparatus.

This laser 19.1 is therefore located outside this housing and it is connected thereto by an optical fibre designated by 19.2.

The diverging beam of coherent light which emerges from this fibre 19.2 is changed into a parallel beam 20 by an optical system 19.3

In addition, the elements of the above-described apparatus are so arranged that the optical axis of the optical system 19.3, which constitutes the emission axis 19a of the generator 19, is parallel to the emission axis 1a of the generator 1.

This parallel beam 20 is directed onto a telescope 21 the optical axis 21a of which is aligned onto the emission axis 19a of the generator 19 and is therefore parallel to the optical axis 3a of the telescope 3.

As in this latter case, the telescope 21 is formed of two optical systems designated by 22 and 23.

A mirror 24 is arranged on the optical path emerging from the telescope 21 so that its plane makes an angle of 45° with the axis 21a and that this beam is reflected in the direction of the axis 3a of the telescope 3.

The axis 24a of the beam reflected by this mirror 24 is thus perpendicular to the optical axis 3a of the telescope 3.

A semi-transparent mirror 25 is arranged between the telescope 3 and the lens 6 so that its plane contains the point of intersection of the axes 3a and 24a, that this plane makes an angle of 45° with these two axes and that the beam reflected by the mirror 24 is again reflected in the direction of the lens 6.

The faces of this semi-transparent mirror 25 are specially treated, in a conventional manner that will not be described here, so that the beam 2 or the beam 9, having passed through the telescope 3, is transmitted in the direction of the lens 6 with as little loss as possible, and that the beam 20, having been reflected by the mirror 24, is again reflected in the direction of this lens 6 also with as little loss as possible.

In the embodiment illustrated in FIG. 4, the optical fibre 8.2 and the optical system 8.3 are arranged so that the axis of the beam emerging from this optical system 8.3 is parallel to the emission axes 1a and 19a of the generators 1 and 19, for reasons which will be set out below.

The emission axis 8a of the generator 8 must nevertheless be perpendicular to the emission axis 1a of the generator 1 so that the beam 9 can be reflected in the direction of the telescope 3 by the mirror 10 when this occupies its position 10b. In this embodiment the generator 8 has a mirror 8.4, the plane of which makes an angle of 45° with the axis of the optical system 8.3 and which is arranged so that the beam emerging from this optical system forms the beam 9 emitted by the generator 8.

It will be seen that in this embodiment shown in FIG. 4 the apparatus of the invention enables the ophthalmologist to perform any desired operation on the eye since it not only has the two generators 1 and 19 which are similar to the generators of known apparatuses, but also the generator 8 which, as in the apparatus of FIG. 1, makes it possible to perform operations in which the treatment beam has to penetrate deep into the tissue of the eye.

In the example illustrated in FIG. 4, the optical systems 8.3 and 19.3 are so designed that the beams 9 and 20 are of the same diameter as the beam 2 and the telescope 21 provides the same widening as the telescope 3. As a result, the angle at the top A of the cone formed by this beam when it is focussed by the lens 6 always has the same value, for example 16°, regardless of the beam used.

It is obvious that, in another embodiment which has not been shown, a system similar to that shown in FIG. 3 can be associated with each of the generators 8 and 19 in order to make it possible to change this angle A.

FIG. 5 illustrates another embodiment of the apparatus of FIG. 4 in which modification of this angle A can be effected more easily, notably thanks to the fact that the optical fibre 8.2 is arranged as shown in this FIG. 4.

In this embodiment, the optical system 8.3 is arranged on a moving support similar to the support 16 of FIG. 3 and designated by 26.

This support 26 is mechanically connected to a motor 27 which can cause it to turn about an axis 26a and adopt one or the other of two predetermined angular positions.

This motor 27 can be controlled by the ophthalmologist using a reversing switch or any other suitable means forming part of a control circuit of the apparatus which has not been shown since its design presents no particular problem.

Figure 5A:
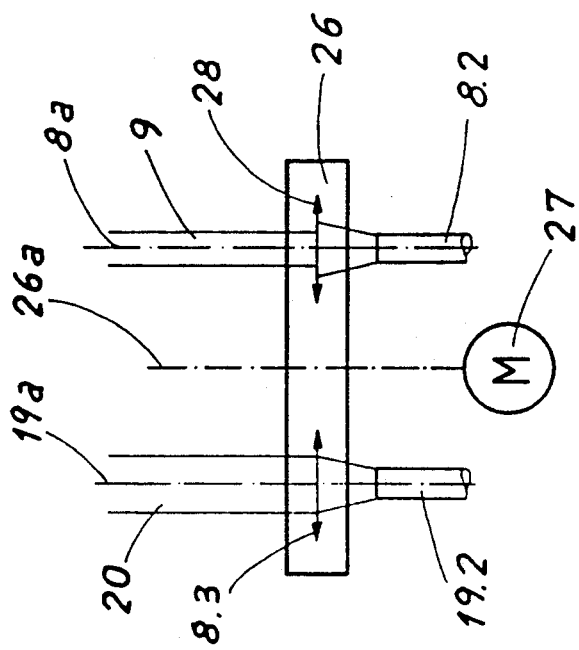
FIGS. 5A and 5B illustrate first and second positions, respectively, of a motor driven optical system for varying the angle "A" of FIG. 4.

The support 26 is so arranged that when it occupies the angular position shown in FIG. 5a, the optical system 8.3 is located opposite the optical fibre 8.2 in the same position as in the case of FIG. 4. The diverging light beam emerging from this fibre 8.2 is therefore also changed into a parallel beam, the diameter of which, which is also the diameter of the beam 9, is the same as in the case of FIG. 4, that is a diameter such that the angle A defined hereinabove is 16°.

A second optical system, designated by 28, is arranged on the support 26 so that, when this latter is in the position shown in FIG. 5a, it is situated opposite the optical fibre 19.2, at the site occupied by the optical system 19.3 in FIG. 4.

The optical system 28 is similar to the optical system 18 in FIG. 3. It consequently changes the diverging beam emerging from the fibre 19.2 into a parallel beam, which is the beam 20 emitted by the generator 19, the diameter of which is such that the angle A referred to hereinabove is 8°.

Figure 5B:
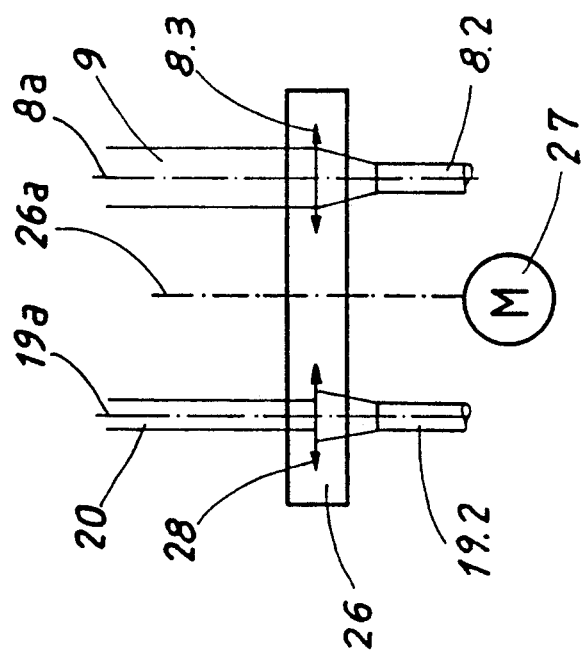

The ends of the optical fibres 8.2 and 19.2 and the support 26 are arranged in relation to each other so that, when this support 26 occupies its second predetermined position, illustrated by the FIG. 5b, it is the optical system 8.3 which is aligned with the optical fibre 19.2 and the optical system 28 which is aligned with the optical fibre 8.2.

It is evident that, in this case, the angle A referred to hereinabove is 8° when the beam 9 is emitted and 16° when the beam 20 is emitted.

The other elements of this embodiment of the apparatus of the invention are identical to those described in connection with FIG. 4, and they are therefore not shown in FIG. 5.

It will be noted that, in the apparatus according to the invention, the presence of a beam switch represented by the mirror 10 in the examples described, as well as the fact that the generators 1 and 8 produce beams of coherent light having the same wavelength, or at least wavelengths close to each other, make it possible to use only one telescope, the telescope 3 in the examples described, to widen the two beams and to direct them onto the lens of the apparatus.

This telescope 3 can thus be designed to transmit these beams in optimum manner with as little loss as possible.

In addition, the fact that the apparatus only has a single telescope for two different beams reduces its price, despite the addition of reversing switches.

As in the case of the optical system 4 of FIG. 1, means can be provided making it possible to move the systems 4 and 22 of the apparatus of FIG. 4 along the axes 3a and 21a respectively to unfocus the treatment beam.

Since these axes 3a and 21a are parallel, these means can comprise a support (not shown) on which are arranged the two optical systems 4 and 22, this support being capable of being shifted sideways parallel to these two axes 3a and 21a.

Numerous modifications may, of course, be made to the apparatus of the invention, notably to the relative position of its various elements, without the apparatus so-modified departing from the scope of the present invention.

It should, however, be noted that of all possible arrangements, the most advantageous are those in which the emission axis 1a of the generator 1 is aligned with the optical axis 3a of the telescope, without any intermediate elements, and in which, when the beam 2 is emitted by the generator 1, the optical switch represented by the mirror 10 occupies a position such that it is situated entirely outside the optical path of this beam 2.

These arrangements are those in which the beam 2, which is the one in which all the light energy is concentrated in very short impulses, encounters the fewest optical elements and thus incurs the least loss.

In common with known apparatuses, the apparatus of the invention preferably has means enabling the ophthalmologist to illuminate and observe the point in the eye which he must treat, as well as means enabling this ophthalmologist to precisely determine, before starting up emission of the treatment beam, the point onto which this beam will be focussed and to check that there is no risk of this treatment beam touching any other part of the eye.

Figure 6:
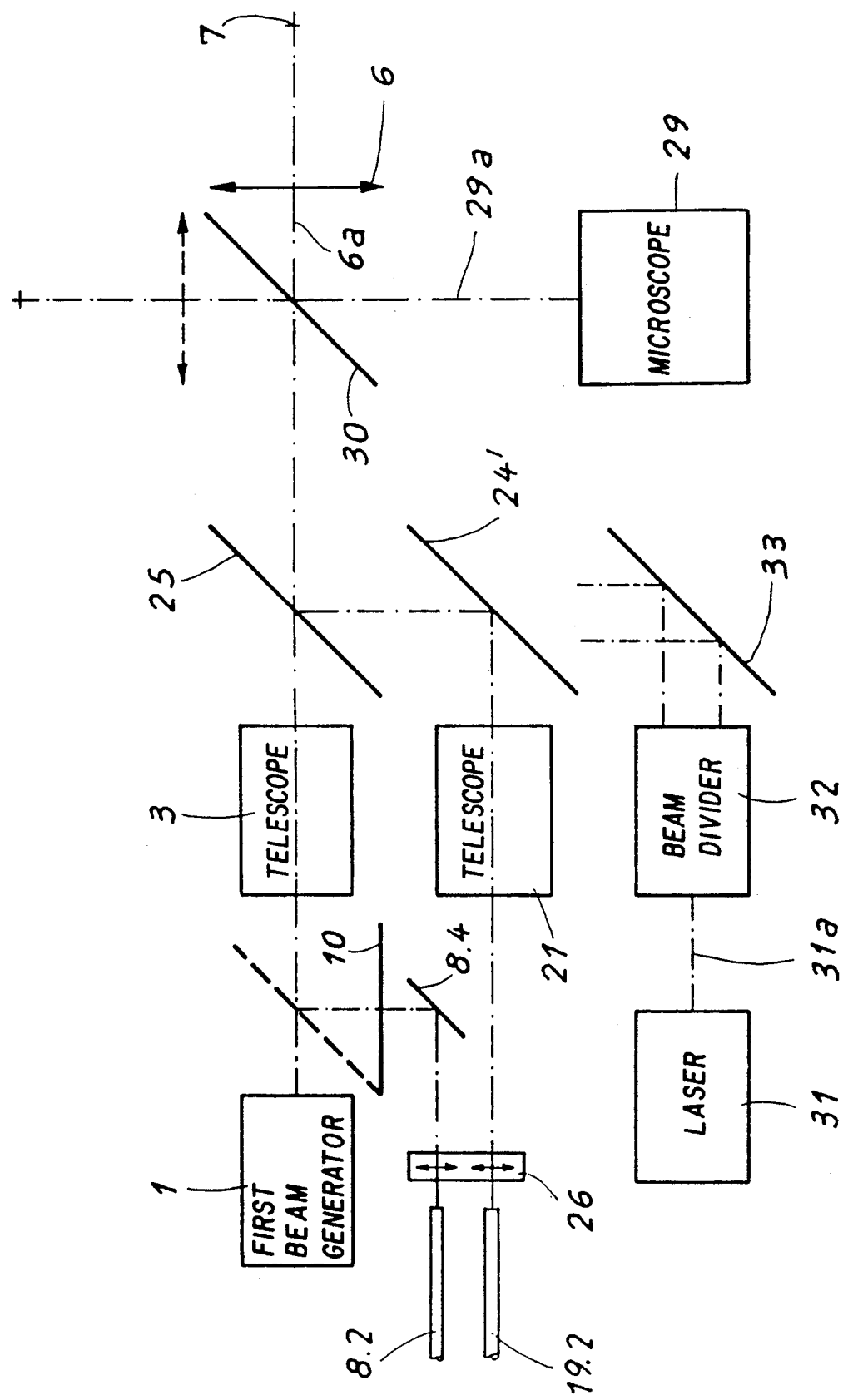
FIG. 6 illustrates another embodiment of the invention including a third beam generator for illuminating the portion of an eye to be treated.

FIG. 6 illustrates an embodiment of the apparatus of the invention having the means just described as well as virtually all the elements described hereinabove with reference to FIGS. 4 and 5.

Of these elements, which have the same reference numerals as in FIGS. 4 and 5 and which will not be described again here, only the mirror 24 has been replaced by a semi-transparent mirror, designated by 24', for reasons to be explained below. Some elements, such as the motors 12 and 27 or the lasers 8.1 and 19.1, have not been shown in this FIG. 6 so as not to confuse it unnecessarily. For the same reason, the different beams of FIGS. 4 and 5, as well as the beams to be described below, are merely symbolized by their axes using a broken, dotted line.

Apart from the elements referred to hereinabove, the apparatus of FIG. 6 has means enabling the ophthalmologist to illuminate and observe the part of the eye requiring treatment.

These means have for example a slit lamp without a reference numeral and a binocular microscope 29 which are well known elements and which will therefore not be described here. The optical axis of this microscope 29, which cuts the axis of the lens 6 at right angles, is designated by 29a.

A semi-transparent mirror 30 is arranged at the intersection of the axes 6a and 29a so that the ophthalmologist can observe through the microscope the area illuminated by the slit lamp.

The semi-transparent mirror 30 is of course treated so as to be as transparent as possible for the treatment beams 2, 9 and 20, and to be as reflecting as possible for the light produced by the slit lamp.

It should be noted that the lens 6 may be arranged so that its optical axis coincides with the axis 29a of the microscope 29, this arrangement, shown with a broken line in FIG. 6, having the advantage that the patient faces the ophthalmologist during treatment.

However, in this case the mirror 30 must of course be designed so as to be as reflecting as possible for the treatment beams 2, 9 and 20, and as transparent as possible for the light produced by the slit lamp.

The apparatus of FIG. 6 also has means enabling the ophthalmologist to precisely determine, before starting up transmission of the treatment beam 2, 9 or 20, the point at which this beam will be focussed and to check that there is no danger of this beam touching any other part of the eye.

Means of this type, which are for example described in patent application EP-A-0 030 210 and will not be described in detail here, have a low-powered laser, designated by 31, which emits a beam of visible light. A laser of this type can be a laser having as active medium a mixture of helium and neon.

This beam is divided into two by an apparatus 32 which has, for example, prisms turning about the emission axis 31a of the laser 31 so that the beams emerging from this apparatus 32 are parallel and define, whilst turning about their axis of symmetry, a cylinder having the same diameter as the treatment beams 2, 9 or 20.

A mirror 33 is arranged so as to reflect these two beams in the direction of the mirror 24', which is a semi-transparent mirror located at the site of the mirror 24 of FIG. 4.

After having crossed this mirror 24', these two beams are reflected by the mirror 25 in the direction of the mirror 30 and of the lens 6.

This latter deviates these two beams so that they intersect at its focal point 7.

Since these beams rotate about their axis of symmetry, they define, between the lens 6 and the focal point 7, a cone which defines the limits of the treatment beam 2, 9 or 20.

We claim:

1. Apparatus for the surgical treatment of a point situated in an eye comprising a first generator means for producing a first beam of coherent light in sucession of energy impulses, each able to produce a microexplosion in a material at said point, an optical means for focusing said first beam on said point, a second generator means for producing a second beam of coherent light capable of penetrating into the thickness of said material, a beam switch means for selectively directing said first beam and said second beam in the axis of said optical system, a third generator means for producing a third beam of coherent light having a wavelength such as to be absorbed by pigments of the blood, means to focus said third beam on said point, and means to change the diameter of said third beam, said means to change the diameter of the third beam comprising a first and second optical element arranged on a common support capable of adopting one or another of two predetermined positions in each of which one of said optical elements is arranged on the path of said third beam, said first and said second optical element being designed so as to give respectively to said third beam a first diameter and a second diameter different from said first diameter.

2. An apparatus according to claim 1, wherein said support and said second and third generators are so arranged that when said support occupies one of said predetermined positions, said first and said second optical element are respectively disposed on the path of said second and said third beam and in which, when said support occupies the other of said predetermined positions, said first and said second optical element are respectively disposed on the path of said third and said second beam.

3. Apparatus for the surgical treatment of a point situated in an eye comprising first generator means for producing a first beam of coherent light in a succession of energy impulses, each able to produce a microexplosion in a material at said point, an optical system means for focusing said first beam along an optical path on said point, a second generator means for producing a second beam of coherent light capable of penetrating into the thickness of said material, a beam switch means for selectively directing said first beam and said second beam in the axis of said optical system, a third generator means for producing a third beam of coherent light having a wavelength such as to be absorbed by pigments of the blood and means for focussing said third beam on said point, said optical system comprising a first telescope and a lens arranged between said telescope and said point to be treated, said means to focus said third beam comprising a semi-transparent mirror, said semi-transparent mirror being mainly transparent for light of said first or said second beam and mainly reflecting for light of said third beam.

4. An apparatus according to claim 3 wherein said beam switch means has a reflecting element having a first position in which said element is situated entirely outside the optical path of said first beam and a second position in which said element reflects said second beam in the direction of said optical system.

5. An apparatus according to claim 3, further comprising means to produce a control signal having a first or a second state, said first generator means including means for responding selectively to said first state of the control signal to produce said first beam, said second generator means including means for responding selectively to said second state of the control signal to produce said second beam and said beam switch means including means for responding selectively to said first and second state of the control signal to direct respectively said first beam and said second beam toward said optical system.

6. An apparatus according to claim 3, further comprising, means for changing the diameter of said second beam.

7. An apparatus according to claim 6 wherein said means for changing the diameter of the second beam comprises a first and a second optical element arranged on a common support capable of adopting one or other of two predetermined positions in each of which one of said optical elements is disposed on the path of said second beam, said first and said second optical element being designed so as to give respectively said second beam a first diameter and a second diameter different from said first diameter.

8. An apparatus according to claim 3 comprising means for changing the diameter of said third beam.

9. An apparatus according to claim 8 wherein said means for changing the diameter of the third beam have a first and a second optical element arranged on a common support capable of adopting one or other of two predetermined positions in each of which one of said optical elements is arranged on the path of said third beam, said first and said second optical element being designed so as to give respectively to said third beam a first diameter and a second diameter different from said first diameter.

10. An apparatus according to claim 9 wherein said support and said second and third generator means are so arranged that when said support occupies one of said predetermined positions, said first and said second optical element are respectively disposed on the path of said second and said third beam and in which, when said support occupies the other of said predetermined positions, said first and said second optical element are respectively disposed on the path of said third and said second beam.

* * * * *